United States Patent [19]

Mulligan

[11] Plant 4,643

[45] Feb. 10, 1981

[54] PLUM TREE

[76] Inventor: James T. Mulligan, 11572 E. Nebraska, Selma, Calif. 93662

[21] Appl. No.: 72,196

[22] Filed: Sep. 4, 1979

[51] Int. Cl.[3] ..... A01H 5/00
[52] U.S. Cl. ..... Plt./38
[58] Field of Search ..... Plt./38

*Primary Examiner*—Robert E. Bagwill
*Assistant Examiner*—James R. Feyrer
*Attorney, Agent, or Firm*—Huebner & Worrel

[57] ABSTRACT

A plum tree which heavily and regularly bears fruit having very dark, almost black, purplish-red skin and which is uniformly of substantially globose shape.

1 Drawing Figure

1

BACKGROUND OF THE NEW VARIETY

The present invention relates to a new and distinct variety of plum tree broadly characterized by its heavy and regular bearing of dark, purplish-red skinned fruit which is uniformly substantially globose in shape, has amber flesh, and ripens in early midseason.

It is well known that purchasers of plums, as with other fruit, are greatly influenced by size, color, and shape of the fruit. There are a number of well-known and successful varieties of plum trees having a purplish-red skin, for example the Damson (unpatented), the El Dorado (unpatented), the Queen Ann (unpatented), and the Nubiana (unpatented). However, the fruit of these varieties is deficient in one or more respects. It is generally small, relatively light in color, ripens late, or is of an unsymmetrical shape. It has long been recognized as desirable to provide a plum tree bearing fruit which is especially dark in color and of pleasing, symmetrical shape and yet is of satisfactory size and date of ripening. Since many varieties of plums of otherwise satisfactory characteristics are notoriously light, and/or irregular bearers of fruit due to difficulties in pollination, it is essential that a plum tree bearing fruit with these desirable qualities also pollinate readily so as to bear such fruit heavily and regularly.

ORIGIN AND ASEXUAL REPRODUCTION OF THE NEW VARIETY

My new variety of plum tree was discovered by me in 1975 in an orchard of Ace plum trees (believed to be unpatented) growing on rootstock propagated from the seeds of seedling peach trees. The orchard was and is owned by me and is located at the corner of Mountain View and Dockery Avenues near the City of Selma, in the County of Fresno, in the State of California. The new variety was discovered as a shoot of new growth from a fallen one of said trees. I cared for the shoot in the expectation that it was of the Ace variety and would supplant the fallen tree, but discovered that the new growth was of a new variety, which is the subject of the present application.

I asexually reproduced the new variety by budding it onto rootstocks of the Marianna (unpatented) and El Dorado (unpatented) varieties of plum trees in an orchard owned by me and located on Nebraska Avenue between Bethel Avenue and Amber Avenue near the City of Selma. The fruit and tree characteristics of plum trees resulting from such budding were identical to those of the original new growth.

2

SUMMARY OF THE NEW VARIETY

The instant variety of plum is generally characterized by bearing fruit having amber flesh and a very dark purplish-red skin, but has important distinctions over other varieties of plum trees bearing fruit having one or more of these general characteristics.

In comparison with the Damson (unpatented) variety, the fruit borne by the new variety is much larger in diameter, has a darker skin and ripens four to six weeks earlier.

In comparison with the Nubiana (unpatented) variety, the fruit of the new variety is similar in size but the fruit of the new variety is substantially globose while the fruit of the Nubiana variety is substantially flattened. The fruit borne by the new variety is further distinguished from that of the Nubiana variety by having a skin color which is slightly darker and by ripening about one week earlier.

In comparison with the El Dorado (unpatented) variety of plum tree, the fruit of the new variety is similar in size, flesh coloration and time of ripening. However, the fruit borne by the El Dorado variety has skin of a deep red color, rather than the very dark, almost black color of the fruit of the new variety.

In comparison with the Simka (Plant Pat. No. 1,882) variety of plum tree, the new variety is distinguished by its bearing of fruit which is somewhat smaller and which has a darker skin coloration, and which is more globose and less pointed than the fruit of the Simka variety.

The fruit borne by the new variety of plum tree has a skin color which is slightly darker than Plate 8-L-7 (Carbuncle +), a flesh color which is substantially that of Plate 11-J-8 (Saratoga), and has axial and transverse dimensions of approximately 4.7 cm. The stone of the new variety adheres to one-half of a cut fruit and becomes free of the other half when the cut fruit is twisted.

The new variety is especially characterized by its bloom and its heavy and regular bearing of fruit due to the ease with which it is self-pollinated.

BRIEF DESCRIPTION OF THE DRAWING

The accompanying drawing is a color photograph of mature plums of the subject variety with one of the plums divided to show the flesh and stone characteristics, together with a typical twig bearing characteristic leaves.

DETAILED DESCRIPTION

Referring more specifically to the pomological details of this new and distinct variety of plum tree, the following has been observed under the ecological conditions prevailing in the designated orchards in Fresno County, Calif. All of the color plate designations are by reference to the Maerz and Paul Dictionary of Color, Second Edition, 1950.

TREE

Size: Medium; Depending upon cultural practices.
Productivity: Heavy and regular bearing.
Trunk: Medium diameter in relation to length.
Branches:

*Current season's growth.*—Size—Medium. Surface texture—Nearly smooth. Color—From 20-L-9 (Eden Green) to near 23-L-5 (Cedar Green). Lenticels—Present on all twigs with secondary growth; small in size and numerous.

*Two year old, spurred.*—Size—Medium. Surface texture—Smooth. Color—Very dark brown, darker than 16-H-12 (Bronzesheen). Lenticels—Moderately numerous, especially below nodes; variable in size; round to coalesced longitudinally in shape.

*Older growth.*—Size—Medium. Surface—Moderately rough with bark in small platelets. Color of mature bark—Plate 15-A-5 (Log Cabin). Lenticels—Color, Plate 13-L-10 (Raw Sienna NA); moderate in number, elongated around branch, medium or slightly larger in size.

Leaves:

*Shoot.*—Size—Medium. Length—10 cm. average. Width—3.8 to 4.0 cm. Shape—Oval to slightly obovate. Color—Ventral surface, Plate 31-E-12; Dorsal surface, Plate 20-E-9. Marginal form—Finely and doubly crenate. Glands—Two to three at apex of petiole. Petiole—Short and stout; length 1.2 to 1.3 cm.; thickness 0.2 cm. Stem glands—Two or three apically disposed, often with two on one side and one on the other side; size, medium large for plum; color, Plate 16-L-12. Stipules—Linear, finely dentate; small in size; one or two in number; often adherent until late July.

*Spur.*—Size—Largest of medium size. Length—Up to 12 cm. Width—3.5 cm. Shape—Long oval to long, slightly obovate; apex accuminate; base long and accuminate. Color—Ventral surface, darker than Plate 24-L-12; dorsal surface, Plate 21-F-6. Marginal form—Very finely crenate. Petiole—Long and slender; length 1:8 to 2.0 cm.; thickness 0.15 cm. Stem glands—Two in number; at apex of petiole or occasionally at base of blade; medium to small in size; globose; color, Plate 16-L-12. Stipules—Lacking.

Buds: Small; plump; glabrous, with many per spur; each bears two to three flowers.

Flowers:

*Dates of bloom.*—In 1979, first bloom on February 28 and full bloom on March 10.

*Sepals.*—Width, at base approximately 2.5 mm.; Length, approximately 3 mm.; oval; glabrous; dorsal surface color, Plate 19-K-7; ventral surface color, Plate 19-K-7 apically, fading to white basally; margin, becomes narrowly rosaceous with age and is minutely dentate apically; dorsal surface, tightly rugose.

*Petals.*—Approximately 9.2 mm. by 7.4 mm.; color white; broad oval and slightly cupped in form with apex rounded and base short to medium accuminate to a short claw; margin, very slightly eroded.

*Pedicel.*—Slender; length 16 to 17 mm.; color, Plate 19-K-6.

*Corolla.*—Form, short funnel to cup; surface texture lightly rugose; color, Plate 19-K-7.

*Pistil.*—One per flower; slender with small capitate stigma; length approximately 10 mm.; color, Plate 19-L-2 (Javel Green).

*Stamens.*—Number, approximately 30; slender, up to 8 mm. in length, longer stamens somewhat longer than pistil; color, white.

*Anthers.*—Fertile, small to medium in size; plump; color, approximately Plate 11-F-10, with reddish streak laterally just before anthesis.

FRUIT

Maturity: Usually matures from July 15 to July 20.

Size: Small/medium to medium; uniform; length, 4.59 ± 0.21 cm.; transverse in suture plane, 4.75 ± 0.18 cm.; transverse at right angle to suture plane 4.71 ± 0.20 cm.; weight 63.50 ± 7.25 grams.

Form: Symmetrical; uniform but slightly irregular; truncate, broad elliptical.

*Suture.*—Usually shallow and rather wide, from base to apex.

*Stem cavity.*—Nearly round to oval; depth, 1.2–1.3 cm.

*Base.*—Slight to medium small; flat; at right angle to axis of fruit.

*Shoulders.*—Rounded to stone cavity; laterally usually somewhat higher; ventrally, depressed as a groove; dorsally, not depressed or slightly depressed.

*Apex.*—Medium in size; depressed; truncate at right angles to axis of fruit.

*Pistil point.*—Very obscure.

*Stem.*—Medium stout and long, length approximately 2.0 cm., caliper 0.2 cm.; color Plate 15-H-12.

*Skin.*—Thin, moderately tough; no apparent tendency to crack.

*Color.*—Slightly darker than Plate 8-L-7 (Carbuncle +).

*Bloom.*—Heavy; color, Plate 39-E-5.

Flesh:

*Color.*—Amber, Plate 11-J-8 (Saratoga); surface of pit cavity, the same or slightly darker.

*Juice.*—Slight when firm ripe.

*Flavor.*—Mild, slightly acid.

*Aroma.*—Lacking.

*Texture.*—Firm, meaty.

*Fibers.*—Lacking.

*Ripening.*—Even.

*Eating quality.*—Fair or better.

Stone:

*Cling characteristics.*—Tight, one-half becomes free when twisting cut fruit, other half adheres.

*Fibers.*—None.

*Size.*—Small; approximately 2.0 cm. long, 1.5 cm. broad, 0.85 cm. thick.

*Form.*—Symmetrical, ovate to broad-ovate.

*Base.*—Small, narrow.

*Surface of sides.*—Nearly smooth.

*Ridges.*—Ventral, narrow and rather sharp; dorsal, low and blunt.

*Grooves.*—Very shallow, nearly obscure.

*Color.*—Approximately Plate 15-L-12 (Raw Umber); lighter at base, apex, and along ventral ridge.

*Splitting tendency.*—None.

Shipping Quality: Good.

Keeping Quality: Good.

Although the new variety of plum tree bears the described characteristics as a result of the growing conditions in Fresno County, Calif., in the central part of the San Joaquin Valley, it is to be understood that variations of the usual magnitude in characteristics incident to growing conditions, fertilization, pruning and pest control are to be expected.

Having thus described and illustrated my new variety of plum tree, what is new and desired to be secured by Letters Patent is:

1. A new and distinct variety of plum tree, substantially as illustrated and described, characterized particularly as to novelty by its heavy bloom and its heavy and regular bearing of fruit which has a very dark, almost black, purplish-red colored skin and which is uniformly of substantially globose form and generally characterized by its bearing of medium sized, amber-fleshed, fruit which ripens in early midseason.

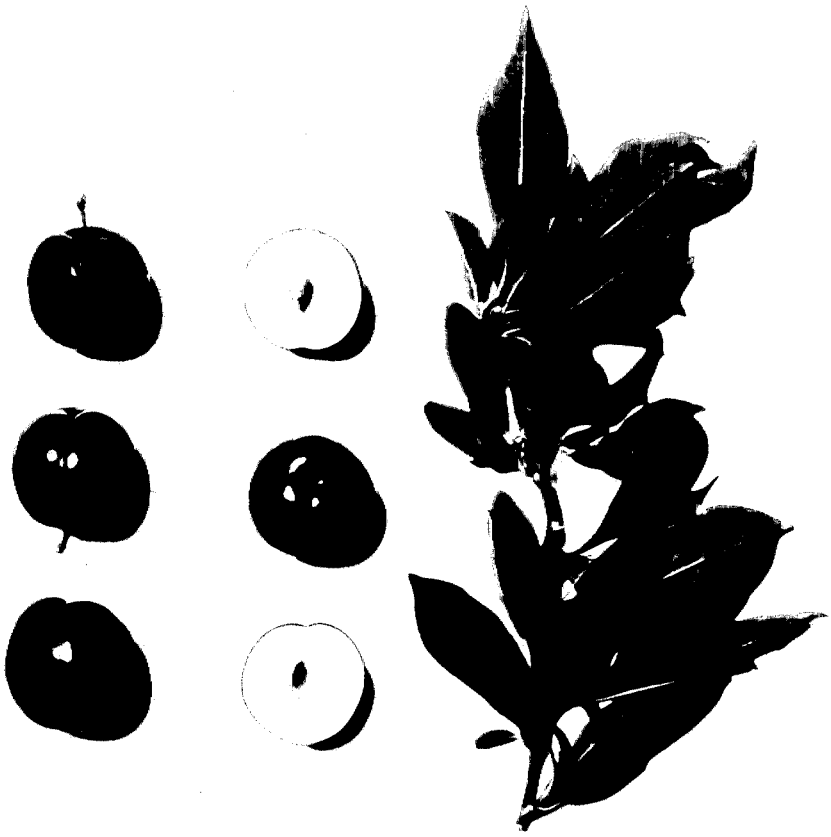

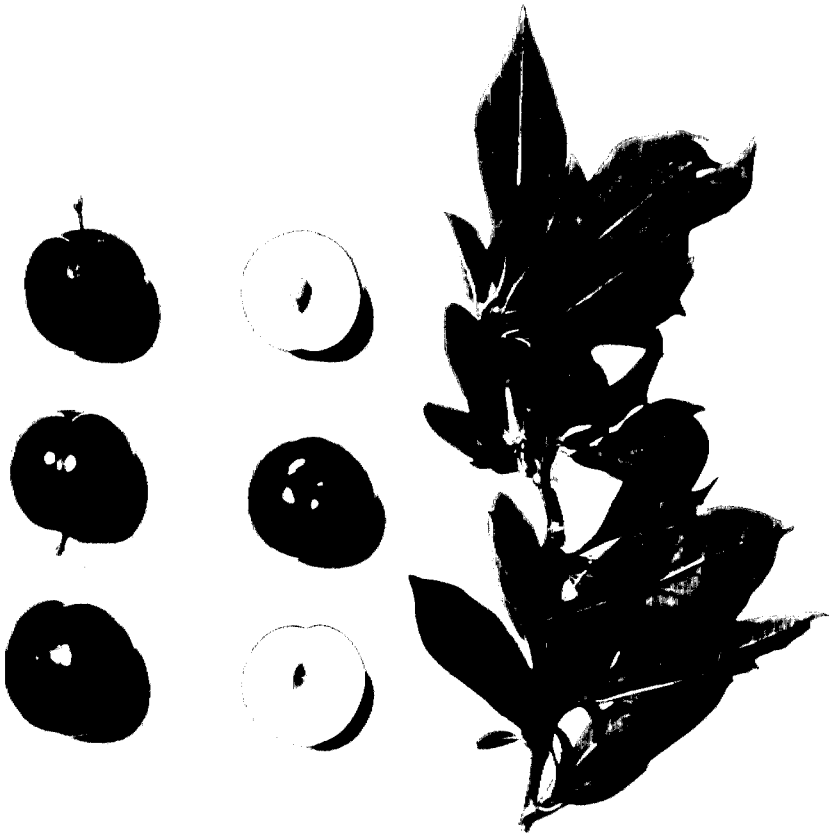

* * * * *